(12) United States Patent
Li et al.

(10) Patent No.: US 8,129,426 B2
(45) Date of Patent: Mar. 6, 2012

(54) WATER-SOLUBLE ARTEMISININ DERIVATIVES, THEIR PREPARATION METHODS, THE PHARMACEUTICAL COMPOSITIONS AND THE USE THEREOF

(75) Inventors: Ying Li, Shanghai (CN); Jianping Zuo, Shanghai (CN); Zhongshun Yang, Shanghai (CN); Junxia Wang, Shanghai (CN); Yu Zhang, Shanghai (CN); Wei Tang, Shanghai (CN); Jianxin Zhang, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 185 days.

(21) Appl. No.: 11/989,135

(22) PCT Filed: Jul. 20, 2006

(86) PCT No.: PCT/CN2006/001782
§ 371 (c)(1),
(2), (4) Date: May 20, 2009

(87) PCT Pub. No.: WO2007/009388
PCT Pub. Date: Jan. 25, 2007

(65) Prior Publication Data
US 2009/0298881 A1    Dec. 3, 2009

(30) Foreign Application Priority Data

Jul. 22, 2005 (CN) .......................... 2005 1 0028056

(51) Int. Cl.
*A61K 31/35* (2006.01)
(52) U.S. Cl. .................................................. 514/450
(58) Field of Classification Search ........................ None
See application file for complete search history.

(56) References Cited

FOREIGN PATENT DOCUMENTS

| CN | 1041595 |   | 4/1990 |
|----|---------|---|--------|
| CN | 1087638 | * | 6/1994 |
| CN | 1296009 |   | 5/2001 |
| CN | 1561994 | * | 1/2005 |

OTHER PUBLICATIONS

Li et al. J. Med. Chem. 2000, 43, pp. 1635-1640.*
Tutor-Ureta et al. (Rev. Clin. Esp. May 2005, 205(5), pp. 230-232).*
Machine translation of Tutor-Ureta et al. (Rev. Clin. Esp. May 2005, 205(5), pp. 230-232). Obtained from <http://www.google.com/translate> Accessed on Oct. 6, 2010.*
Wang et al. Br. J. Pharmacol. Mar. 2008 153(6): pp. 1303-1310.*
International Search Report for PCT/CN2006/001782 mailed Nov. 16, 2006.
International Preliminary Report on Patentability for PCT/CN2006/001782, Nov. 21, 2007.
Written Opinion of the International Searching Authority for PCT/CN2006/001782, Nov. 16, 2006.

* cited by examiner

*Primary Examiner* — Rebecca Anderson
*Assistant Examiner* — Alicia L Otton
(74) *Attorney, Agent, or Firm* — McKenna Long & Aldridge LLP

(57) ABSTRACT

Water-soluble artemisinin derivatives, their preparation methods, the pharmaceutical compositions containing the same derivatives and the use thereof are disclosed. The artemisinin derivatives have following formula I. It has been proved by pharmacological tests that these compounds and compositions have evident immuno-suppressive activities, and may be used in the preparation of novel immuno-suppressants for treating the diseases caused by hyperfunction of human immunity (e.g. the auto-immune diseases such as lupus erythematosus, rheumatoid arthritis, multiple sclerosis and the like), and for inhibiting the graft rejection after cell or organ transplantation.

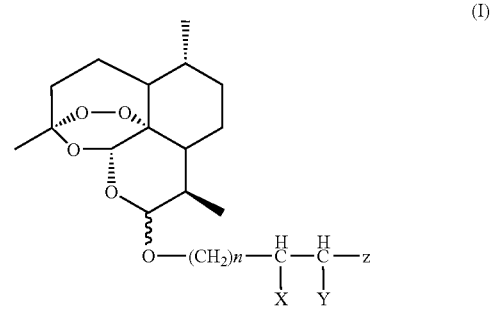

(I)

2 Claims, 2 Drawing Sheets

WATER-SOLUBLE ARTEMISININ DERIVATIVES, THEIR PREPARATION METHODS, THE PHARMACEUTICAL COMPOSITIONS AND THE USE THEREOF

CROSS-REFERENCE TO RELATED APPLICATIONS

This application is the National Phase of PCT/CN2006/001782, filed 20 Jul. 2006, which designated the U.S. and claims priority to Chinese Patent Application No. 200510028056.9, filed 22 Jul. 2005, the entire contents of each of which are hereby incorporated by reference.

TECHNICAL FIELD

The present invention relates to the chemosynthesis of terpenoid compounds and the immune inhibiting effect thereof, especially to novel artemisinin compounds, the preparation methods thereof, and the pharmaceutical compositions thereof as immunosuppressant.

BACKGROUND ART

Artemisinin is an antimalarial principle extracted from the traditional Chinese Medicine Qinghao (*Artemisia annua* L.), and is a peculiar sesquiterpene lactone having a peroxy group. It has not only excellent antimalarial activity but also immunosuppressive effect. Its derivative, artesunate, possesses more powerful immune inhibiting effect than artemisinin and may be used to treat lupus erythematosus and some kinds of dermatoses effectively [YU Qibin et al., 56 Cases of Lupus Erythematosus Treated by Artesunate, Chinese Journal of Dermatology, 1997, 39: 51; Chen Hua et al., Clinical Observation on the Treatment for Eczema-Dermatitis and Photosensitivity Dermatosis with Artesunate, Bengbu Medical College Academic Journal, 1991, 16: 251]. But the patients must suffer a long-term intravenous injection, and the solution of sodium artesunate must be prepared just before injection, thus it is very inconvenient in use. Currently, the immunosuppressant used commonly in clinic, cyclosporin A, is expensive and toxic to kidney and liver, so that some patients can not persist in the treatment. Therefore, the present inventors conduct a study for more effective and safer immunosuppressants.

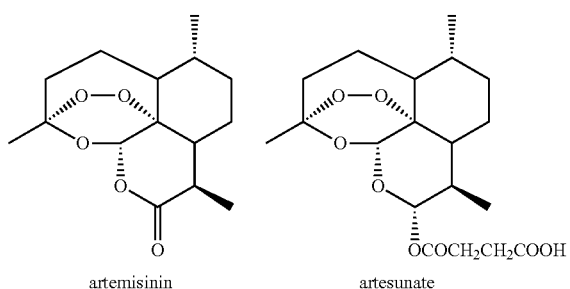

artemisinin     artesunate

The present inventors have discovered that a category of artemisinin derivatives containing a carboxylic acid group has a better immune inhibiting effect (Chinese Patent Application No.: 200510023824.1). However, they have sparing solubility in water, and probably poor bioavailability thereby. Thus, the present inventors continued to searching for more ideal immunosuppressants.

DISCLOSURE OF THE INVENTION

One object of the present invention is to provide a category of water-soluble artemisinin derivatives.

Another object of the present invention is to provide processes for their preparation.

Still another object of the present invention is to provide their medical use.

Still another object of the present invention is to provide their pharmaceutical compositions.

The present invention provides a compound represented by following formula (1), the isomers and pharmaceutic salts thereof:

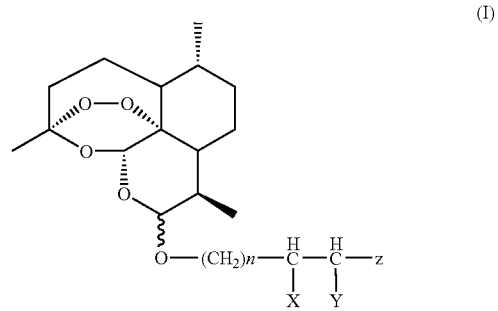

(I)

In the formula (1), when n=0, X and Y is H, and Z is $NH_2$;

when n=1, X is OH, Y is H, and Z is $NH_2$, NHMe, NHEt, NHPr(n), NHBu, $NHCH_2CH_2OH$,

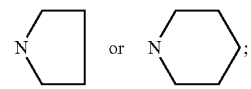

when n=1, X is OH, Y is $CH_3$ or phenyl, etc, and Z is $NH_2$, NHR, $NHCH_2CH_2OH$, $NR'_2$, $NH(CH_2)_{2-3}NMe_2$,

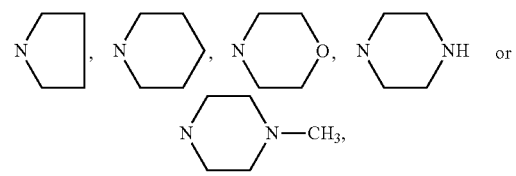

wherein, R and R' is a $C_1$-$C_4$ alkyl.

The isomers of the compound represented by formula (1) include, but do not limit to, the stereoisomers and optical isomers.

The pharmaceutic salts of the compound represented by formula (1) include, but do not limit to, the addition salts with hydrochloric acid, methanesulfonic acid, p-toluenesulfonic acid, maleic acid, oxalic acid, tartaric acid, citric acid, etc.

Preferably, the compounds represented by formula (1) of the present invention are the following compounds:

n=0, X and Y is H, and Z is $NH_2$; or n=1, X is OH, Y is H, and Z is $NHC_4H_9(t)$, or

The present invention provides processes for preparation of the compound represented by formula (1), the isomers and pharmaceutic salts thereof, in which the dihydroartemisinin is used as raw material to react with a substituted alcohol under an acidic catalysis condition. If the substituted alcohol is a haloalcohol, then the product further reacts with ammonia to produce the target compound represented by formula (1) (n=0). If the substituted alcohol is a dihydric alcohol, then the produced hydroxyl-arteether is converted into the p-toluene-sulfonate and further reacts with ammonia to produce the target compound represented by formula (1) (n=0). If the substituted alcohol is glycidol, the obtained glycidyl artemisinin ether reacts with amines to produce the target compounds represented by formula (1) (n=1). And if the substituted alcohol is propenol, the product is further oxidized into glycidyl artemisinin ether, and then reacts with amines to obtain the target compounds represented by formula (1) (n=1). The target compounds, free base, may react with an organic acid or an inorganic acid in organic solvent, such as alcohol etc., to produce corresponding salts. The compounds represented by formula (1) produced according to the method of the present invention may be refined through the conventional processes.

Some detailed processes for preparation may refer to the previous patents of the same inventors (CN 89109562.4, CN 93112454.9) and the published paper (J. Med. Chem. 2000, 43 (8): 1635-1640).

The present invention further provides pharmaceutical compositions having an immune inhibiting effect which contain the compound of formula (1) or its pharmaceutically acceptable salts in a safe and effective dose range and the pharmaceutically acceptable carriers.

The "safe and effective dose" means that the amount of the compound is sufficient to evidently improve the patients' condition but will not cause a serious side effect. The safe and effective dose of the compound is determined according to the specific conditions, such as the age and weight of the subject, the adaptive diseases, the route of administration, the course of treatment and any other related therapy, etc. Generally, an adult is administered by 10 mg/day to 800 mg/day in a single dose or multiple doses. The dosage should be reduced accordingly for children. The formulation of the said pharmaceutical composition is as following:

| | |
|---|---|
| Artemisinin ether containing amino group (measured by weight percent) | 1-55% |
| Excipient (measured by weight percent) | 15-40% |
| Auxiliary agent (measured by weight percent) | 20-65% |

The composition of the present invention can be administered through oral, parenteral, pernasal, perlingual, transocular, per respiratory tract or per rectum routines, especially as tablet or enteric coatel pill, injection water solution, sublingual tablet, patch, suppository, cream, ointment, gels for skin use, etc.

"Pharmaceutically acceptable carrier" means one or more compatible solid or liquid fillers or excipients, which are suitable for human body and must have sufficient high purity and low toxicity. "Compatible" herein means that each component of the composition can be blended with the compound of the present invention or with each other without remarkably reducing the pharmacodynamic activity of the compound. Some examples of pharmaceutically acceptable carrier includes sugars (e.g. glucose, sucrose, lactose, etc.), starch (e.g. maize starch, potato starch, etc.), cellulose and its derivatives (e.g. sodium carboxymethy cellulose, sodium ethyl cellulose, cellulose acetate, microcrystalline cellulose, etc.), polyethylene glycol, glutin, talc powder, stearic acid, magnesium stearate, calcium sulphate, vegetable oil (e.g. soybean oil, sesame oil, peanut oil, olive oil, etc.). It also may be emulsifier (e.g. Tween®), moistening agent (e.g. sodium dodecyl sulphate), coloring agent, flavoring agent, stabilizer, preservative, nonpyrogenic water, etc. The selection of carriers for the compound of the present invention depends on the administration mode of the compound.

The inventors screened and studied the compounds of the present invention on their immunosuppressive activity in vitro and in vivo with the following methods (reference book: Modern Pharmacological Experimental Methods, Zhang Juntian ed., Beijing Medical University/Chinese Peking Union Medical University Union Press, 1998).

1. Experimental Materials

Experimental animals: inbred Balb/c male mice, 6-8 weeks old.

RPMI-1640 culture solution (Roswell Park Memorial Institure-1640 medium, from GibcoBRL, Life Technologies, USA) with 10% fetal bovine serum (FBS), 100 U/mL penicillin, 100 μg/mL streptomycin, 10 mM HEPES (4-(2-hydroxyethyl)-1-piperazineethane sulfonic acid) and 50 μM 2-ME (2-Mercaptoethanol).

Stimulant: Concanavalin (ConA), and bacterial Lipopolysaccharide (LPS, from *Escherichia Coli* 055: B5), diluted with RPMI-1640 culture solution to suitable concentration before using.

2. Experimental Methods

[1] Lymphocytotoxicity Test

1) Mice were killed by cervical dislocation, and their spleens were collected aseptically and levigated to form a single cell suspension; after removing erythrocytes with MTT solution (10% SDS (Sodium dodecyl sulfate) and 50% dimethylformamide, pH 7.2), the cell concentration was adjusted to $5 \times 10^6$/mL with RPMI-1640 medium containing 10% FBS.

2) 80 μL cell suspension, 40 μL testing sample, 40 μL medium containing 10% FBS were added into a 96 well culturing plate; and the blank control group was set by adding 80 μL medium to total volume of 160 μL.

3) The cell culture was incubated in 5% $CO_2$ incubator at 37° C. for 48 hours, and 16 μL MTT (5 mg/mL) was added into each well 6-7 hours before the termination of the incubation.

4) When the incubation was terminated, 80 μL MTT solution (10% SDS, 50% dimethylformamide; pH7.2) was added into each well, and after placed in incubator for 6-7 hours, $OD_{570}$ values was measured with a microplate reader at 570 nm.

[2] Lymphocyte Proliferation Test

1) Mice were killed by cervical dislocation, and their spleens were collected aseptically and prepared into a single cell suspension. The cell concentration was adjusted to $4 \times 10^6$/mL with RPMI-1640 medium containing 10% FBS.

2) 100 μL cell suspension, 50 μL testing sample solution, 50 μL ConA or LPS solution were added into a 96-well plate, and for the control group, 50 μL medium containing 10% FBS was added. The total volume was 200 μL.

3) The cell culture was incubated in 5% $CO_2$ incubator at 37□ for 48 hours, and 0.5 μCi [$^3$H]-thymidine (25 μL/well) was added into each well 7-8 hours before the termination of the incubation.

4) After the incubation was terminated, the cells were harvested on a glassfiber film with a cell harvestor (HARVESTER96®, TOMTEC), and after scintillation fluid was added, the incorporation of [$^3$H]-thymidine in the cell DNA was measured with a liquid scintillation counter (MicroBeta Trilux®, PerkinElmer) to indicate the state of cell proliferation.

[3] Homologous and Heterogeneous Mixed Lymphocyte Proliferation Reaction (MLR)

1) C57BL/6 and Balb/c mice were killed by cervical dislocation, and their spleens were collected aseptically and levigated into a single cell suspension. After removing the erythrocytes, the cell concentration was adjusted to $6 \times 10^6$/mL with RPMI-1640 medium containing 10% FBS.

2) The spleen cells of C57BL/6 mice as the response cells and the spleen cells of Balb/c mice (irradiated with Co60, 3000 rads) as the stimulus cells were mixed in equal volumes.

3) 100 μL cell mixture, 100 μL testing sample were added into a 96-well plate. For the control group, 100 μL medium containing 10% serum was added. And single culture controls of the two kinds of cells were set.

4) The cell cultures were incubated in 5% $CO_2$ incubator at 37□ for 3, 4 or 5 days. 25 μL $^3$H diluent (i.e. $3.8 \times 10^{10}$ Bq [$^3$H]-thymidine) was added one day before the termination of the incubation.

5) After the incubation was terminated, the plate was freezed in a −20□ refrigerator.

6) The cells were harvested on a glassfiber film with a cell harvestor (HARVESTER96', TOMTEC), and the incorporation of [$^3$H]-thymidine in DNA was measured with a liquid scintillation counter (MicroBeta Trilux®, PerkinElmer) to indicate the state of cell proliferation.

[4] Delayed Hypersensitive Response Animal Model (DTH)

1) The sensitization was induced by topical application of 20 μL of 0.5% (v/v) DNFB in acetone: olive oil (4:1) onto each rear paw of mice on day 0 and 1;

2) Excipient and testing compounds were given by the oral route 1 day before challenge and then once a day for 2 days (days 8-10);

3) The mice were challenged by application of 10 μL of 0.5% (v/v) DNFB on the inner and outer surfaces of the right ear on day 9;

4) The increase in the ear patch weight (8-mm punches) and ear thickness between the left and right ear was measured 30-48 h after challenge.

[5] Mice Arthritis Model Induced by Bovine Collagen Type II

Bovine collagen type II (CII, Collagen Research Center, Tokyo, Japan) was dissolved in 0.1N acetum and placed in a 4□ refrigerator overnight. On the experiment day, DBA/1 mice were immunized at the tail base with 125 μg of collagen emulsified in Freund's complete adjuvant (CFA) containing *Mycobacterium tuberculosis* strain H37Rv (Wako Pure Chemical Industries Ltd., Osaka, Japan) and boosted with the same preparations of collagen plus CFA 3 weeks later, but IFA was used as an adjuvant this time. One day before the reimmunization, the testing sample was administrated (i.p or intragastric) and the administration continued for 2 weeks to 3 months. The experiment result was evaluated according to the following scores: 0: no reddish and swelling; 1: slightly swelling on toe joint; 2: swelling on toe joint and sole; 3: swelling on paw below ankle joint; 4: swelling on whole paw including ankle joint. The total scores of four limbs for each animal represented the severity of CIA (collagen-induced arthritis).

3. Experimental Results

[1] Lymphocyte Proliferation and Lymphocytotoxicity Tests

The immune response activity mainly includes the cellular immunity mediated by T cells and the humoral immunity mediated by B cells. The inhibitory effect of a drug on lymphocyte proliferation was evaluated with cell activation, division and proliferation when stimulating the cells directly with the T-cell mitogen ConA and the B-cell mitogen LPS in vitro. Firstly, the compounds were screened repeatedly on three concentrations of 10 μm, 1 μm and 0.1 μm. Among other things, the compounds of examples 1, 11 and 14 showed obvious immune inhibitory activities with a concentration without any cytotoxicity, and their inhibiting rates to T-cell proliferation (Con A) were 65%, 48% and 52% respectively, their inhibiting rates to B-cell proliferation (LPS) were 73%, 99% and 81% respectively. In addition, the compounds of example 2, 3 and 12, with a concentration without any cytotoxicity, had the inhibiting rates to T-cell proliferation (Con A) of 48%, 47% and 47% respectively and the inhibiting rates to B-cell proliferation (LPS) of 48%, 51% and 47% respectively; the compounds of example 8, 16, 17 and 18, with a concentration without any cytotoxicity, had the inhibiting rates to T-cell proliferation (Con A) of 13%, 0%, 6% and 9% respectively and the inhibiting rates to B-cell proliferation (LPS) of 42%, 51%, 24% and 26% respectively, this result indicated that these four compounds had a stronger inhibiting activity for B-cell proliferation, but less or no inhibiting activity for T-cell proliferation with a concentration without any cytotoxicity. Based on the above results, the compounds of example 1, 11 and 14 were selected to be further experimented on their pharmacological activity of immunodepression in vitro and in vivo.

[2] Homologous and Heterogeneous Mixed Lymphocyte Proliferation Reaction (MLR)

The alloantigen is the main factor causing the rejection reaction of organism after blood transfusion and organ transplantation. When the response lymphocytes are cultured together with heterogenous lymphocytes, the alloantigen expressed on the heterogenous lymphocytes mainly are the histocompatibility antigen MHC-I and MHC-II molecules, which stimulate the response T cells to induce the immune proliferation reaction. The pharmacologic effect of drugs on immune system response, which is more resemble to the physiological conditions, is evaluated by the effect of the drugs on MLR. As shown in figures, the compounds of examples 1, 11 and 14 remarkably inhibited the proliferation of the response lymphocytes in MLR, and their EC50 values are 3.48±0.72 μM, 0.59±0.066CM and 0.67±0.012 μM respectively.

[3] Delayed Hypersensitive Response Animal Model (DTH)

The classical mice DTH response model was employed to further examine the immune pharmacological activity of the compounds of examples 1, 11 and 14 in vivo. The results showed that the compounds of examples 1, 11 and 14 could obviously inhibit the swelling of the ear of mice (p<0.01) when being administered orally with an amount of 50 mg/kg, 100 mg/kg and 50 mg/kg respectively, and their inhibiting rates were 56.5%, 50.5% and 52.2% respectively compared with the control group, which is comparative with the pharmacological activity of cyclosporine A(CsA) (5 mg/kg), an inhibiting rate of 40.6%.

[4] Mice Arthritis Model

The compounds of example 1 and example 14 were further tested of the immune pharmacological activity in the mice arthritis model. The results indicated that the compounds of example 1 and example 14 could obviously reduce the swelling of the mice' joints (p<0.05) when being taken orally with an amount of 1 mg/kg and 0.5 mg/kg respectively.

EMBODIMENTS OF THE INVENTION

Figure 1:
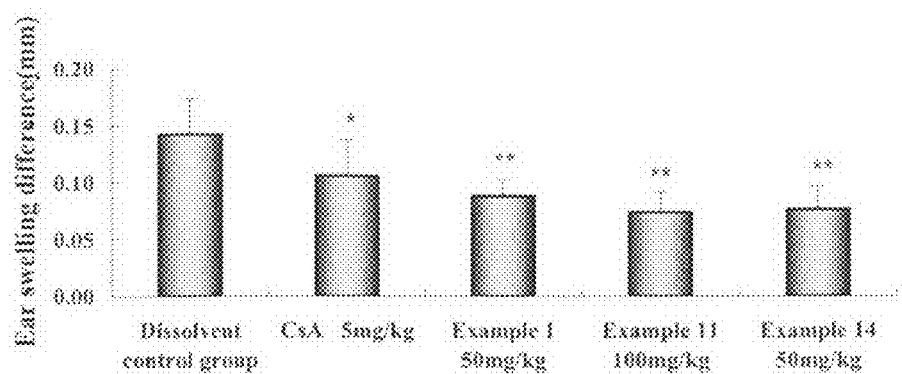
FIG. 1 is a graph showing the thickness difference of swelling on ears, in which the compounds of example 1, example 11 and example 14 obviously reduced the swelling degree on ears of the DTH mice.
Figure 2:
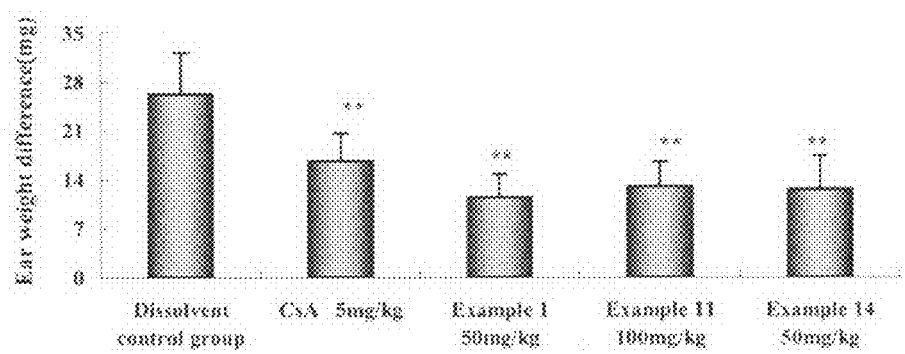
FIG. 2 is a graph showing the weight difference of ear slices, in which the compounds of example 1, example 11 and example 14 obviously reduced the weight of swelling ears of the DTH mice.
Figure 3:
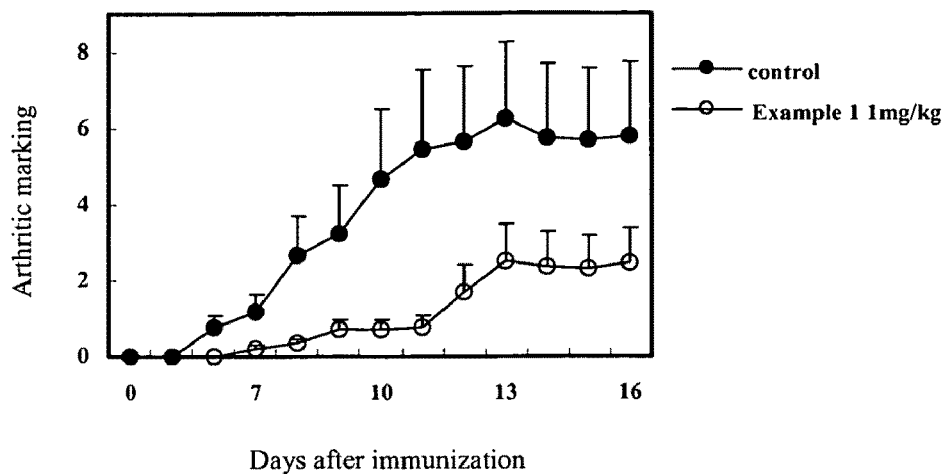
FIG. 3 is a graph showing the scorings of the arthritis degree with and without the compound of example 1, which indicates the compound of example 1 can prevent and cure the mice arthritis induced by bovine collagen type II and inhibit the swelling of the sicked joints.
Figure 4:
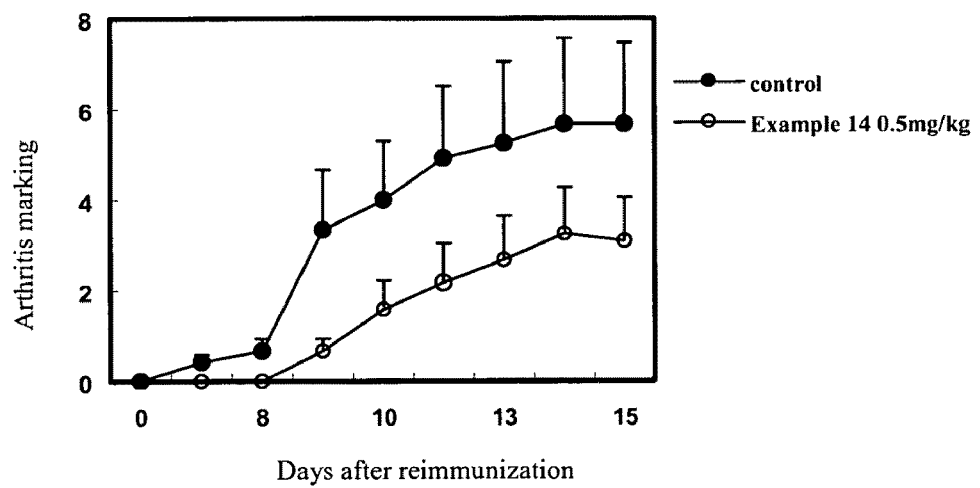
FIG. 4 is a graph showing the scorings of the arthritis degree with and without the compound of example 14, which indicates the compound of example 14 can prevent and cure the mice arthritis induced by bovine collagen type II and inhibit the swelling of the sicked joints.

Hereinafter, the present invention will be explained with reference to the examples, but these examples are not construed to limit the present invention in any way. (The compositions in following examples are measured by weight percent.)

In the following examples, the artemisinin nucleus is represented by Q:

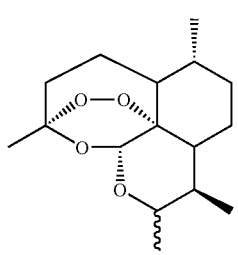
(Q)

the ripple line ( ∿ ) represents β substitution or/and a substitution;
the solid line ( ▬ ) represents β substitution;
the dash line ( ▪▪▪▪ ) represents a substitution.

Example 1

2'-amino arteether (β type)

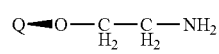

forming a salt with maleic acid. White crystal. Melting point: 139-141□.
Elemental analysis ($C_{21}H_{33}NO_9$):

| Calculated values: | C 56.87 H 7.50 N 3.16 |
| Measured values: | C 56.84 H 7.59 N 3.10. |

Example 2

3'-amino-2'-hydroxy-artemisinin propyl ether (β type)

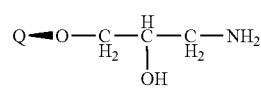

forming a salt with maleic acid. White crystal. Melting point: 146-147□.
Elemental analysis ($C_{22}H_{35}O_{10}N$):

| Calculated values: | C 55.80 H 7.45 N 2.96 |
| Measured values: | C 55.92 H 7.43 N 2.94. |

Example 3

3'-methylamino-2'-hydroxy-artemisinin propyl ether (β type)

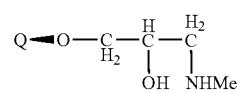

forming a salt with maleic acid. White crystal. Melting point: 145-146□.
Elemental analysis ($C_{23}H_{37}O_{10}N$):

| Calculated values: | C 56.66 H 7.65 N 2.87 |
| Measured values: | C 56.67 H 7.63 N 2.89. |

Example 4

3'-methylamino-2'-hydroxy-artemisinin butyl ether (β type)

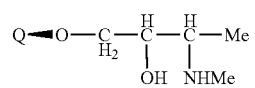

forming a salt with maleic acid. White amorphous solid.
Elemental analysis ($C_{24}H_{39}O_{10}N$):

| Calculated values: | C 57.47 H 7.84 N 2.79 |
|---|---|
| Measured values: | C 57.72 H 7.66 N 2.67. |

Example 5

3'-amino-2'-hydroxy-artemisinin butyl ether (β type)

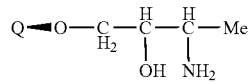

forming a salt with maleic acid. White amorphous solid. Elemental analysis ($C_{23}H_{37}O_{10}N$):

| Calculated values: | C 56.66 H 7.65 N 2.87 |
|---|---|
| Measured values: | C 56.64 H 7.74 N 2.71. |

Example 6

3'-hydroxyethylamino-2'-hydroxy-artemisinin propyl ether (β type)

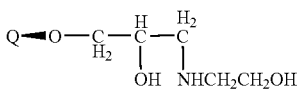

forming a salt with maleic acid. White amorphous solid. Elemental analysis ($C_{24}H_{39}O_{11}N$):

| Calculated values: | C 55.70 H 7.59 N 2.71 |
|---|---|
| Measured values: | C 55.69 H 7.89 N 2.58. |

Example 7

3'-phenyl-3'-methylamino-2'-hydroxy-artemisinin propyl ether (β type)

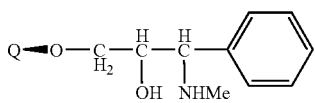

forming a salt with maleic acid. White amorphous solid. Elemental analysis ($C_{29}H_{41}O_{10}N$):

| Calculated values: | C 61.80 H 7.33 N 2.49 |
|---|---|
| Measured values: | C 61.64 H 7.41 N 2.48. |

Example 8

3'-phenyl-3'-amino-2'-hydroxy-artemisinin propyl ether (β type)

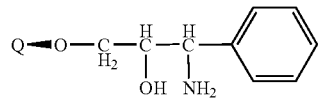

forming a salt with maleic acid. White amorphous solid. Elemental analysis ($C_{28}H_{39}O_{10}N$):

| Calculated values: | C 61.19 H 7.15 N 2.55 |
|---|---|
| Measured values: | C 61.29 H 7.23 N 2.35. |

Example 9

3'-hydroxyethylamino-2'-hydroxy-artemisinin butyl ether (β type)

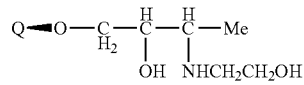

forming a salt with maleic acid. White amorphous solid. Elemental analysis ($C_{25}H_{4}O_{10}N$):

| Calculated values: | C 56.49 H 7.77 N 2.63 |
|---|---|
| Measured values: | C 56.21 H 7.94 N 2.95. |

Example 10

3'-dimethylamino-2'-hydroxy-artemisinin butyl ether (β type)

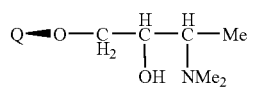

forming a salt with maleic acid. White amorphous solid. Elemental analysis ($C_{25}H_{41}O_{10}N$):

| Calculated values: | C 58.24 H 8.02 N 2.72 |
|---|---|
| Measured values: | C 58.06 H 7.99 N 2.67. |

Example 11

3'-pyrrolidinyl-2'-hydroxy-artemisinin propyl ether (β type)

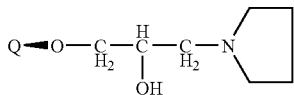

forming a salt with maleic acid. White crystal. Melting point: 158-160□.
(As reported in J. Med. Chem. 2000, 43(8): 1635-1640, the melting pointing of the said compound was 148-152□.)
Elemental analysis ($C_{26}H_{41}O_{10}N$):

| Calculated values: | C 59.19 H 7.83 N 2.65 |
|---|---|
| Measured values: | C 59.14 H 7.86 N 2.66. |

Example 12

3'-piperidyl-2'-hydroxy-artemisinin propyl ether (β type)

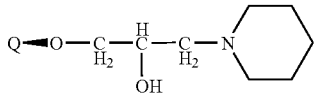

forming a salt with maleic acid. White crystal. Melting point: 157-1590.
Elemental analysis ($C_{27}H_{43}O_{10}N$):

| Calculated values: | C 59.87 H 8.00 N 2.59 |
|---|---|
| Measured values: | C 59.86 H 8.02 N 2.58. |

Example 13

3'-methylamino-2'-hydroxy-artemisinin butyl ether (α type)

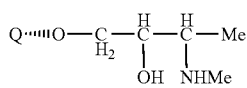

forming a salt with maleic acid. White amorphous solid.
Elemental analysis ($C_{24}H_{39}O_{10}N$):

| Calculated values: | C 57.47 H 7.84 N 2.79 |
|---|---|
| Measured values: | C 57.62 H 7.51 N 2.61. |

Example 14

3'-tert-butylamino-2'-hydroxy-artemisinin propyl ether (β type)

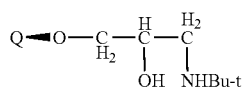

forming a salt with maleic acid. White crystal. Melting point: 171-173□.
Elemental analysis ($C_{26}H_{43}O_{10}N$):

| Calculated values: | C 58.96 H 8.18 N 2.64 |
|---|---|
| Measured values: | C 58.92 H 7.91 N 2.59. |

Example 15

3'-phenyl-3'-pyrrolidinyl-2'-hydroxy-artemisinin propyl ether (β type)

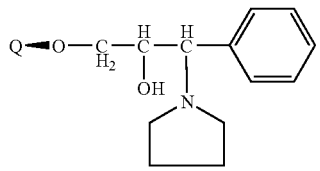

forming a salt with maleic acid. White amorphous solid.
Elemental analysis ($C_{32}H_{45}O_{10}N$):

| Calculated values: | C 63.67 H 7.51 N 2.32 |
|---|---|
| Measured values: | C 63.36 H 7.09 N 2.04. |

Example 16

3'-phenyl-3'-piperidyl-2'-hydroxy-artemisinin propyl ether (β type)

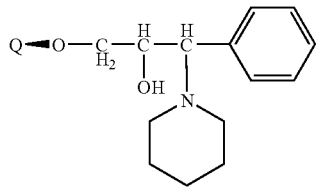

forming a salt with maleic acid. White crystal. Melting point: 163-165□.
Elemental analysis ($C_{33}H_{47}O_{10}N$):

| | |
|---|---|
| Calculated values: | C 64.16 H 7.67 N 2.27 |
| Measured values: | C 64.43 H 7.68 N 2.18. |

Example 17

3'-phenyl-3'-dimethylamino-2'-hydroxy-artemisinin propyl ether (β type)

$$Q\text{---}O\text{---}\underset{H_2}{C}\text{---}\underset{OH}{\overset{H}{\underset{|}{C}}}\text{---}\underset{NMe_2}{\overset{H}{\underset{|}{C}}}\text{---}\text{Ph}$$

forming a salt with maleic acid. White crystal. Melting point: 166-168□.

Elemental analysis ($C_{30}H_{43}O_{10}N$):

| | |
|---|---|
| Calculated values: | C 62.38 H 7.50 N 2.42 |
| Measured values: | C 62.05 H 7.68 N 2.41. |

Example 18

3-phenyl-3'-tert-butylamino-2'-hydroxy-artemisinin propyl ether (β type)

$$Q\text{---}O\text{---}\underset{H_2}{C}\text{---}\underset{OH}{\overset{H}{\underset{|}{C}}}\text{---}\underset{NHBu\text{-}t}{\overset{H}{\underset{|}{C}}}\text{---}\text{Ph}$$

forming a salt with maleic acid. White crystal. Melting point: 167-169□.

Elemental analysis ($C_{32}H_{47}O_{10}N$):

| | |
|---|---|
| Calculated values: | C 63.45 H 7.82 N 2.31 |
| Measured values: | C 63.70 H 7.83 N 2.22. |

Example 19

A tablet containing 2'-amino-arteether (β type) maleate
The formula is as follows:

| | |
|---|---|
| 2'-amino-arteether (β type) maleate | 35% |
| Starch | 25% |
| Sodium hydroxylmethyl cellulose | 30% |
| Starch paste (10%) | 9% |
| stearic acid | 1% |

The active component was pulverized, and screened with 100 mesh sieve; after mixed with sodium hydroxylmethyl cellulose and 10% starch paste, granulation and drying were carried out. Then the dry starch and lubricant was added into and mixed uniformly; tabletting was performed to obtain the final product.

Example 20

A tablet containing 3'-tert-butylamino-2'-hydroxy-artemisinin propyl ether (β type) maleate
The formula is as follows:

| | |
|---|---|
| 3'-tert-butylamino-2'-hydroxy-artemisinin propyl ether (β type) maleate | 30% |
| Microcrystalline cellulose | 65% |
| Micronized polyethylene glycol 4000 | 5% |

The active component was pulverized and screened; after mixed uniformly with microcrystalline cellulose and lubricant, tabletting was performed immediately to obtain the final product.

Example 21

An enteric coated tablet containing 2'-amino-artemether (β type) citrate
The formula is as follows:

| | |
|---|---|
| 2'-aminoartemether (β type) citrate | 35% |
| Starch | 20% |
| Dry starch | 35% |
| Starch paste (10%) | 8% |
| Talc powder | 2% |

The active component was mixed uniformly with starch, and 10% starch paste was added to prepare the damp mass, then granulation, drying, and pelletization are processed. After dry starch and talc powder were further added, tabletting and coating with an enteric coating were performed to obtain the final product.

Example 22

A hard capsule containing 3'-pyrrolidinyl-2'-hydroxy-artemisnin propyl ether (β type) oxalate
The formula is as follows:

| | |
|---|---|
| 3'-tetrahydropyrrole-2'-hydroxyartemisic propyl ether (β type) oxalate | 50% |
| Microcrystalline cellulose | 30% |
| Polyethylene glycol 1500 | 20% |

The active component and the auxiliary materials are homogeneously mixed and packed into empty capsula to obtain the final product.

Example 23

A gel containing 3'-pyrrolidinyl-2'-hydroxy-artemisinin propyl ether (β type)

The formula is as follows:

| | |
|---|---|
| 3'-pyrrolidinyl-2'-hydroxy-artemisinin propyl ether (β type) | 35% |
| polyethylene glycol | 65% |

Polyethylene glycol 300 and polyethylene glycol 1500 (polyethylene glycol 300:polyethylene glycol 1500=1:1) were agitated and heated to be molten, then the active component after being pulverized and sieved was added, and mixed homogenously to obtain a gel product.

Example 24

An water injection solution containing 2'-amino-artemether (β type) maleate

After the active component was dissolved in water, filtration, encapsulation and sterilization were performed to obtain the final product.

The invention claimed is:

1. A method of treating lupus erythematosus or rheumatoid arthritis, comprising administering to a subject in need of same an effective amount of a water-soluble artemisinin compound of the following formula:

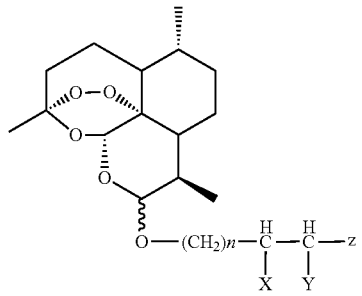

wherein, n=0 or 1; and when n=0, X and Y are H, and Z is $NH_2$;

when n=1, X is OH, Y is H, and Z is $NH_2$, NHMe, NHEt, NHPr(n), NHBu, $NHCH_2CH_2OH$,

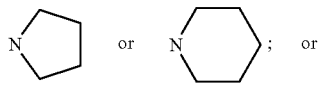; or when n=1, X is OH, Y is $CH_3$ or phenyl, and Z is $NH_2$, NHR, $NHCH_2CH_2OH$, $NR'_2$, $NH(CH_2)_{2-3}NMe_2$,

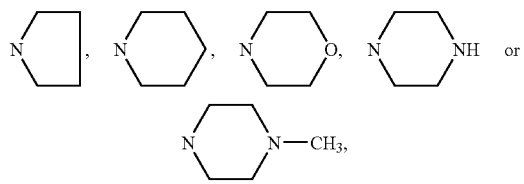

wherein R and R' are independently C1-C4 alkyl, and the stereoisomers, optical isomers, and pharmaceutically acceptable salts thereof.

2. The method of claim 1, wherein the water-soluble artemisinin compound is selected from the group consisting of 2'-amino arteether (β type) and 3'-tert-butylamino-2'-hydroxy-artemisinin propyl ether (β type), and the stereoisomers, optical isomers, and pharmaceutically acceptable salts thereof.

* * * * *